(12) United States Patent
Yan

(10) Patent No.: US 6,238,864 B1
(45) Date of Patent: May 29, 2001

(54) ANALYTE DETECTION ASSAY AND METHODS OF USE

(75) Inventor: Lin Yan, St. Paul, MN (US)

(73) Assignee: Bio-Seek, Inc., Minnetonka, MN (US)

( * ) Notice: Subject to any disclaimer, the term of this patent is extended or adjusted under 35 U.S.C. 154(b) by 0 days.

(21) Appl. No.: 09/118,256

(22) Filed: Jul. 17, 1998

Related U.S. Application Data

(60) Provisional application No. 60/053,164, filed on Jul. 18, 1997.

(51) Int. Cl.[7] .............................. C12Q 1/68; G01N 33/53; G01N 33/567; C07K 1/00
(52) U.S. Cl. ...................... 435/6; 435/91.2; 435/69.1; 435/7.1; 435/7.21; 435/325; 530/350
(58) Field of Search ........................... 435/6, 69.1, 7.1; 530/350

(56) References Cited

U.S. PATENT DOCUMENTS 5,604,101 * 2/1997 Hanley et al. ............................ 435/6
5,955,595 * 9/1999 Korsmeyer ............................ 536/23.5

OTHER PUBLICATIONS

Blau, J. et al., "Three Functional Classes of Transcriptional Activation Domains", *Mol. and Cell Biol.*, 16(5):2044–55 (1996).
Chasman, D.I. et al., "GAL4 Protein: Purification, Association with GAL80 Protein, and Conserved Domain Structure", *Mol. and Cell. Biol.*, 10(6):2916–23 (1990).
Chi et al., "The ZEBRA Activation Domain: Modular Organization and Mechanism of Action", *Mol. and Cell. Biol.*, 13:7045–55 (1993).
Dove, S.L. et al. "Activation of prokaryotic transcription through arbitrary protein —protein contacts", *Nature*, 386:627–30, (1997).
Estojak, J. et al., "Correlation of Two–Hybrid Affinity Data with In Vitro Measurements", *Mol. Cell. Biol.*, 15(10):5820–9 (1995).
Farmer, G. et al. "Functional Interaction between p53, the TATA–Binding Protein (TBP), and TBP–Associated Factors In Vivo", *Mol. and Cell Biol.*, 16(8): 4295–340 (1996).
Fields, S. et al., "The Two–hybrid system: an assay for protein–protein interactions", *TIG*, 10(8):286–92 (1994).
Fields et al., "A novel genetic system to detect protein–protein interactions", *Nature*, 340:245–6 (1989).
Flanagan, P.M. et al., "Resolution of Factors Required for the Initiation of Transcription by Yeast RNA Polymerase II", *J. Biol. Chem.*, 265(19):11105–7 (1990).
Guadreau, L. et al. "RNA Polymerase II Holoenzyme Recruitment Is Sufficient to Remodel Chromatin at the Yeast PH05 Promoter", *Cell*, 89:55–62, (1997).
Hermanson, G. "Contents Overview", *Bioconjugate Techniques*. 1996. Academic Press, New York.
Hippenmeyer, P. et al., "Enhancing expression of recombinant proteins in mammalian cells using the herpesvirus VP16 transactivator", *Current Opinion in Biotech*, 6:548–52 (1995).
Horikoshi, M. et al., "Mechanism of Action of a Yeast Activator: Direct Effect of GAL4 Derivatives on Mammalian TFIID–Promoter Interactions", *Cell*, 54:665–9 (1988).

(List continued on next page.)

Primary Examiner—Kenneth R. Horlick
Assistant Examiner—Joyce Tung
(74) Attorney, Agent, or Firm—Mueting, Raasch & Gebhardt, P.A.

(57) ABSTRACT

Provided herein is an assay for the detection of an analyte and a method therefore. The assay and method depend upon detecting the binding of an analyte to a capturing agent positioned on DNA through the production of a reporter. The assay and the method of the invention are simple because the assay can be conducted in a single tube, sensitive because concentrations of both the activator complex and the DNA construct drive the analyte-recognition reaction, and readily adaptable for automation.

36 Claims, 5 Drawing Sheets

OTHER PUBLICATIONS

Ikeda, R.A. et al., "In Vivo and in Vitro Activities of Point Mutants of the Bacteriophage T7 RNA Polymerase Promoter", *Biochemistry*, 31:9073–9080 (1992).

Ikeda, R.A., et al., "Interactions of the RNA polymerase of bacteriophage T7 with its promoter during binding and initiation of transcription", *Proc. Natl. Acad. Sci.*, 83:3614–3618 (1986).

Johnston, S.A. et al., "Interaction of Positive and Negative Regulatory Proteins in the Galactose Regulon of Yeast", *Cell*, 50(1):143–6 (1987).

Leibowitz, et al., "In Vitro Protein Synthesis", *Methods in Enzymology*, 194:536–544 (1991).

Lin Y–S et al., "GAL4 Derivatives Function Alone and Synergistically with Mammalian Activators In Vitro", *Cell*, 54:659–64 (1988).

Lin Y–S et al., "Mechanism of Action of an Acidic Transcriptional Activator In Vitro", *Cell*, 64:971–81 (1991).

Lohr, D. et al., "Transcriptional regulation in the yeast GAL gene family: a complex genetic network", *FASEB J.*, 9:777–87 (1995).

Lue, N.F. et al., "Accurate initiation at RNA polymerase II promoters in extracts from *Saccharomyces cerevisiae*", *Proc. Natl. Acad. Sci. USA*, 84:8839043 (1987).

Lue, N.F. et al., "RNA Polymerase II Transcription in Vitro" *Methods in Enzymol.*, 194:545–50 (1991).

Ohashi, Y. et al., "Modulating the Potency of an Activator in a Yeast In Vitro Transcription System", *Mol. and Cell. Biol.*, 14(4):2731–9 (1994).

Osumi–Davis, P.A. et al., "Bacteriophage T7 RNA Polymerase and Its Active–site Mutants", *J. Mol. Biol.*, 237:5–19 (1994).

Phizicky, E. et al., "Protein–Protein Interactions: Methods for Detection and Analysis", *Microbiol. Rev.*, 59:94–123 (1995).

Ptashne, M. and Gann A., "Transcriptional activation by recruitment", *Nature*, 386(6625):569–77, (1997).

Schick, C. et al., "Tests of a Model of Specific Contacts in T7 RNA Polymerase—Promoter Interactions", *Biochemistry*, 34:666–672 (1995).

Sousa, R. et al., "Model for the Mechanism of Bacteriophage T7 RNAP Transcription Initiation and Termination", *J. Mol. Biol.*, 224:319–334 (1992).

Tantin, D. et al., "Biochemical Mechanism of Transcriptional Activation by GAL4–VP16", *Methods in Enzymology*, 274:133–149, (1996).

Weston, B.F., et al., "Positioning of the Start Site in the Initiation of Transcription by Bacteriophage T7 RNA Polymerase" *J. Mol. Biol.*, 272:21–30 (1997).

Woontner, M. et al., "Accurate Initiation by RNA Polymerase II in a Whole Cell Extract from *Saccharomyces cerevisiae*", *J. Biol. Chem.*, 265(16):8979–82 (1990).

Ayoubi et al., "A Nonradioactive Method to Determine Levels of in Vitro Transcription in Nuclear Extracts," *Analytical Biochemistry*, 225, 190–192 (1995).

Ayoubi et al., "Regulation of gene expression by alternative promoters," *The FASEB Journal*, 10, 453–460 (1996).

Christopoulos et al., "Expression Immunoassay. Antigen Quantitation Using Antibodies Labeled with Enzyme–Coding DNA Fragments," *Anal. Chem.*, 67, 4290–4294 (1995).

* cited by examiner

: may be antibody or antigen

ANALYTE DETECTION ASSAY AND METHODS OF USE

This application claims the benefit of U.S. Provisional Patent Application, Ser. No. 60/053,164, filed Jul. 18, 1997.

FIELD OF THE INVENTION

This invention relates to the general field of diagnostic assays and to methods for detecting the presence of analyte in a sample and to methods for generating signals in diagnostic assays.

BACKGROUND OF THE INVENTION

Diagnostic assays are assays to test for the presence of an analyte in a test sample. Typically, diagnostic assays are immunoassays, that is, they involve the detection, of or exploit the use of, antibody molecules. Immunoassays are analytical tests that rely on the specificity of the reaction between antibodies and antigens to measure the concentration of either an antigen or an antibody in a sample of interest. In its simplest form, an immunoassay is the reaction of soluble antibody with soluble antigen and the product of the immunoassay is a measurement of the amount of antibody or antigen reacting with a known or constant amount of antigen or antibody, respectively. A variety of immunoassays are known in the art and more sophisticated immunoassays with increased assay sensitivity use magnifiers, amplifiers, or indicators, so that smaller quantities of antigen or antibody can be measured. The most commonly used immunoassays take advantage of the properties of certain enzymes. When the antibodies are linked to an enzyme, enzymatic activity serves as a marker for antibody binding.

Immunoassays can be accomplished using a variety of formats to meet different requirements such as sensitivity, simplicity, and/or feasibility of automation, and the like. These formats can be categorized into two general groups: heterogeneous or homogenous immunoassays. Heterogeneous systems are generally more sensitive, but usually require a series of washing steps to separate free from bound analyte (i.e., the molecule to be detected, whether antibody, antigen, or the like). Most commercially available immunoassay systems are heterogeneous because assays that are of high sensitivity, low background and low cost are preferred. The typical steps for performing a common heterogeneous immunoassay includes a coating step; that is, the immobilization of antigen or capturing antibodies onto a solid carrier. Next there are washing steps, incubation of the coated surface with sample, more washing steps, incubation with one or more detecting antibodies, signal amplification and development. The whole procedure takes several hours to several days to complete, and efficient automated systems are not available for these assays. High sensitivity for analyte in the assays is often achieved using sensitive enzymatic labels such as luciferase, alkaline phosphatase, galactosidase, and the like. Sensitive labels can reach a level of sample detection of less than $10^{-21}$ mol, with a potential to reach the limit of the antibody's affinity under optimized conditions (usually around $10^{-15}$ to $10^{-16}$ mol of analytes).

Homogenous immunoassays, on the other hand, are immunoassays where both the binding reaction and the detection and/or quantitation of the reaction are performed in solution without separating the free from the bound components. The sensitivity of the homogenous immunoassay is reduced as compared with a heterogeneous format. Homogenous immunoassays can be classified into two major types: competitive and noncompetitive binding immunoassays. Competitive assays usually include antigen labeled with enzyme or enzyme modulators (e.g., an inhibitor, activator, allosteric effector, or the like). The assay is typically based on a competitive reaction of antibody with antigen labeled with enzyme (conjugate) and antigen in present in the sample. The enzyme activity linked to the antigen is either inhibited or activated when the conjugate forms an immunocomplex with antibody. While it is relatively simple, these assays have several disadvantages. In general, the assays are insensitive as compared to heterogenous assays. Homogenous assay sensitivity depends on the concentration of the conjugate. In addition, homogenous assays can be inefficient at detecting high molecular weight antigens. On the other hand, antibody labeled with enzyme is used in noncompetitive binding assays based on either substrate "channeling", caused by close contact of two enzymes, or the modulation of enzyme activity due to binding of antigen to the conjugate. This format is more sensitive than a competitive assay; however, the assay format is still less sensitive than heterogeneous systems since, in general, either the concentration of the conjugate cannot be lower than a certain limit or the final signal detection is based on loss of activity rather than gain of activity. In addition, homogenous assays tend to have a higher noise to signal ratio than noncompetitive immunoassays.

Recent immunoassay developments focus on assay sensitivity, simplicity and assay automation. Homogenous systems are useful since multiple handling steps are typically not required making them particularly adaptable to automation. As noted, homogenous assay sensitivity is somewhat reduced as compared with heterogenous assay formats. For example, in homogenous immunoassays, an increase in assay sensitivity can be achieved by decreasing the amount of antigens or antibodies in the assay. Both antigen and antibody are labeled with enzyme in the reaction system but there is a level to which the antibody or antigen can be reduced and still generate a finctional assay. Most commercially available homogenous assays use competitive formats with sensitivities ranging in the microgram to nanogram levels. The analytes detected in these assays are limited to haptens and low-molecular-weight substances. Homogenous systems are not commercially available for high-molecular-weight proteins.

SUMMARY OF THE INVENTION

Thus, there remains a need for an in vitro kit and a method that are sensitive, simple, can detect relatively large molecular weight analytes, and suitable for automation.

One aspect of the present invention provides a method for detecting analyte in a sample. Another aspect of the present invention provides an in vitro kit that is suitable for detecting the binding of an analyte to a capturing agent positioned on DNA through the production of a reporter.

A method in accordance with the present invention preferably includes the steps of adding a sample to a sample reservoir, wherein the reservoir comprises: (a) an isolated DNA fragment comprising a capturing agent linked to DNA, wherein the DNA comprises at least one promoter and at least one reporter DNA; (b) reagents including those suitable for supporting transcription from a DNA fragment; and (c) an activator complex comprising an activator and an analyte recognizing region. The method then includes the steps of incubating the sample in the reservoir for a time sufficient to generate transcription of the at least one reporter DNA to produce reporter RNA; and detecting the presence of reporter RNA in the reservoir wherein the presence of reporter RNA indicates that analyte is present in the sample. The reagents may further include those suitable for supporting translation.

The term "analyte" refers to a molecule that is to be measured or detected in the assay of this invention. Preferably the analyte is an antibody; an antigen, including molecules capable of being recognized by antibodies such as haptens, proteins (including polypeptides and peptides), lipids, sugars, nucleic acids or drugs; and/or a ligand or a receptor. The term "capturing agent" refers to any molecule, usually a protein or nucleic acid capable of specifically recognizing the analyte in solution.

The term "promoter" used herein refers to a specific nucleotide sequence to which RNA polymerase, which may include a mutation, and, optionally, regulatory protein(s), bind to initiate transcription.

The term "reporter" refers to nucleic acid capable of being transcribed into RNA where the RNA or the protein translated therefrom can be detected in solution and where the presence of the RNA or protein is evidence of the binding of the analyte to the capturing agent.

The term "activator complex" is used herein to refer to a complex comprising a transcriptional activator linked to an analyte recognizing region such as a molecule that is capable of specifically recognizing analyte at a site that does not compete for binding with the site on the capturing agent that recognizes analyte.

Preferably, the detecting step further includes translating reporter RNA into protein and the sample reservoir further comprises reagents suitable for supporting translation of reporter RNA.

The term "transcription" is used herein to refer to the synthesis of RNA from a DNA template, wherein the synthesized RNA is complementary to the strand of DNA from which it was synthesized.

The term "translation" is used herein to refer to the synthesis of a polypeptide chain from an RNA template.

In one embodiment of the present invention, the promoter is a eukaryotic promoter and the reagents are those suitable for supporting transcription from eukaryotic DNA. In another embodiment of the present invention, the promoter is a prokaryotic promoter and the reagents are those suitable for supporting transcription from prokaryotic DNA.

The term "eukaryote" is used herein to refer to an organism which contain a compartmentalized internal structure in which different cellular functions are carried out in membrane-bound organelles, e.g., nucleus, mitochondria, chloroplast, endoplasmic reticulum, Golgi apparatus, etc. The term "prokaryote" is used herein to refer to a single celled organism with a relatively simple internal structure lacking in organelles, wherein the DNA is not enclosed in a nucleus (as opposed to a eukaryote).

The method may include the detecting step which detects RNA produced from the reporter. Further, the method may include the detecting step which further includes detecting protein produced from the RNA.

The capturing agent preferably includes a moiety selected from the group consisting of an antibody, a variable binding domain of an antibody, a binding domain of an antibody receptor, or a combination thereof. The analyte recognition region of the activator complex may also include a moiety selected from the group consisting of an antibody, a variable binding domain of an antibody, a binding domain of an antibody receptor, or a combination thereof Preferably, the analyte includes a peptide.

In another embodiment, the capturing agent includes a peptide. Accordingly, the analyte preferably includes a peptide recognition moiety selected from the group consisting of an antibody, a variable binding domain of an antibody, a binding domain of an antibody receptor, or a combination thereof.

Another aspect of the present invention provides in vitro kit for the detection of an analyte which includes reagents comprising those that are suitable for supporting transcription from a DNA fragment; an isolated DNA fragment comprising a capturing agent linked to a DNA, wherein the DNA comprises at least one promoter and at least one reporter DNA; an activator complex comprising an activator and an analyte recognition region; and at least one reaction reservoir.

The reagents may also include those that are suitable for supporting translation. They can be those that are suitable for supporting eukaryotic translation, those that are suitable for supporting prokaryotic translation, or a combination thereof Preferably, the DNA comprises two copies of a promoter linked to a reporter DNA, wherein one copy is oriented opposite the other copy. More preferably, one copy of the promoter linked to the reported DNA is separated from the other copy by a restriction endonuclease adaptor site. Preferably, the capturing agent and the promoter are separated by a distance in the range of about 20 base pairs to about 500 base pairs. The capturing agent and the promoter are separated by a distance in the range of about 20 base pairs to about 500 base pairs. The capturing agent may include a moiety selected from the group consisting of an antibody, a variable binding domain of an antibody, a binding domain of an antibody receptor, or a combination thereof. The analyte recognition region may include a moiety selected from the group consisting of an antibody, a variable binding domain of an antibody, a binding domain of an antibody receptor, or a combination thereof. Preferably, the capturing agent comprises a peptide.

Yet another aspect of the present invention provides a method for detecting analyte in a sample which includes the steps of adding a sample to a sample reservoir. Preferably, the reservoir contains an isolated DNA fragment comprising a capturing agent linked to DNA, wherein the DNA comprises at least one prokaryotic promoter and at least one reporter DNA; reagents comprising those suitable for supporting transcription from a DNA fragment; and a complex comprising an analyte recognizing region and a bacteriophage polymerase. The method also includes the steps of incubating the sample in the reservoir for a time sufficient to generate transcription of the at least one reporter DNA to produce reporter RNA; and detecting the presence of reporter RNA in the reservoir wherein the presence of reporter RNA indicates that analyte is present in the sample.

A further aspect of the present invention provides an in vitro kit for the detection of an analyte which includes reagents comprising those that are suitable for supporting transcription from a DNA fragment; an isolated DNA fragment comprising a capturing agent linked to a DNA, wherein the DNA comprises at least one prokaryotic promoter and at least one reporter DNA; a complex comprising an analyte recognition region and a bacteriophage polymerase; and at least one reaction reservoir.

Preferably, the prokaryotic promoter comprises a nucleotide sequence having at least one point mutation deactivating bacteriophage polymerase binding activity of the prokaryotic promoter, which can be selected from the group consisting of T3 promoter, T7 promoter, and SP6 promoter.

The reagents may further comprise those suitable for supporting translation. Similarly, the detecting step further comprises translating reporter RNA into protein and the sample reservoir further comprises reagents suitable for supporting translation of reporter RNA.

DETAILED DESCRIPTION OF THE PREFERRED EMBODIMENTS

In a preferred aspect of this invention, the invention relates to a method for the detection of an analyte in a sample. The method employs DNA, preferably a DNA, that comprises a capturing agent positioned on the DNA, at least one regulatory region, such as a promoter, capable of promoting transcription from a reporter, and a reporter capable of being transcribed to RNA when the promoter is activated. Preferably, the DNA also includes an adaptor nucleotide sequence, wherein at least a portion converts one restriction endonuclease site to another, a portion that encodes an RNA transcript signal (e.g., a poly A tail or a TATA signal), and, optionally, a portion that encodes a promoter. Examples include SEQ ID NO:1, SEQ ID NO:2, SEQ ID NO:3, and SEQ ID NO:4. SEQ ID NO: 1 and SEQ ID NO:2 each include a portion that converts an Xba I restriction site to a BamHI and a portion that encodes a poly A tail. SEQ ID NO:3, and SEQ ID NO:4 each include a portion that converts a Hind III restriction site to an Eco RI site, a portion that includes a TATA signal, and a portion that encodes an Elb minimal promoter. Other adaptor nucleotide sequences can be designed by those skilled in the art.

The assay further comprises an activator complex. The activator complex includes an activator that is capable of facilitating RNA polymerase-mediated transcription from the reporter in the presence of a suitable promoter. The activator complex also includes an analyte recognizing region that is capable of specifically recognizing the analyte in the assay. Preferred transcriptional activators are gal4 (Fields S and Song O-K, *Nature* 340:245–6, 1989), ZEBRA (Chi T. and Carey M., *Mol. and Cell. Biol.* 13:7045–55, 1993), and VP16 (Tantin D. et al. *Methods in Enzymology.* 274:133–149, 1996) for eukaryotic-based systems and λcI-CTD for a prokaryotic system (Dove SL et al. *Nature* 386:627–30, 1997), such as a system using a prokaryotic promoter including those found in bacteria such as *E coli*. Transcriptional activators of this invention also include artificial transcriptional activators such as synthesized small peptides including GAL4-AH as described by Lin Y-S et al. (supra) and Chasman (supra). Other transcriptional activators that could be tested in this assay include, but are not limited to, the activation domains of a variety of transcriptional factors such as jun, fos, myc, and ela. These factors are known and have been described in the art. In the assay of this invention, the capturing agent on the DNA is sufficiently close to the promoter such that when the analyte, present in a fluid sample, contacts the capturing agent, and the analyte binds to the activator complex via the analyte recognizing region, an RNA polymerase is capable of directing transcription of the reporter.

Figure 1:
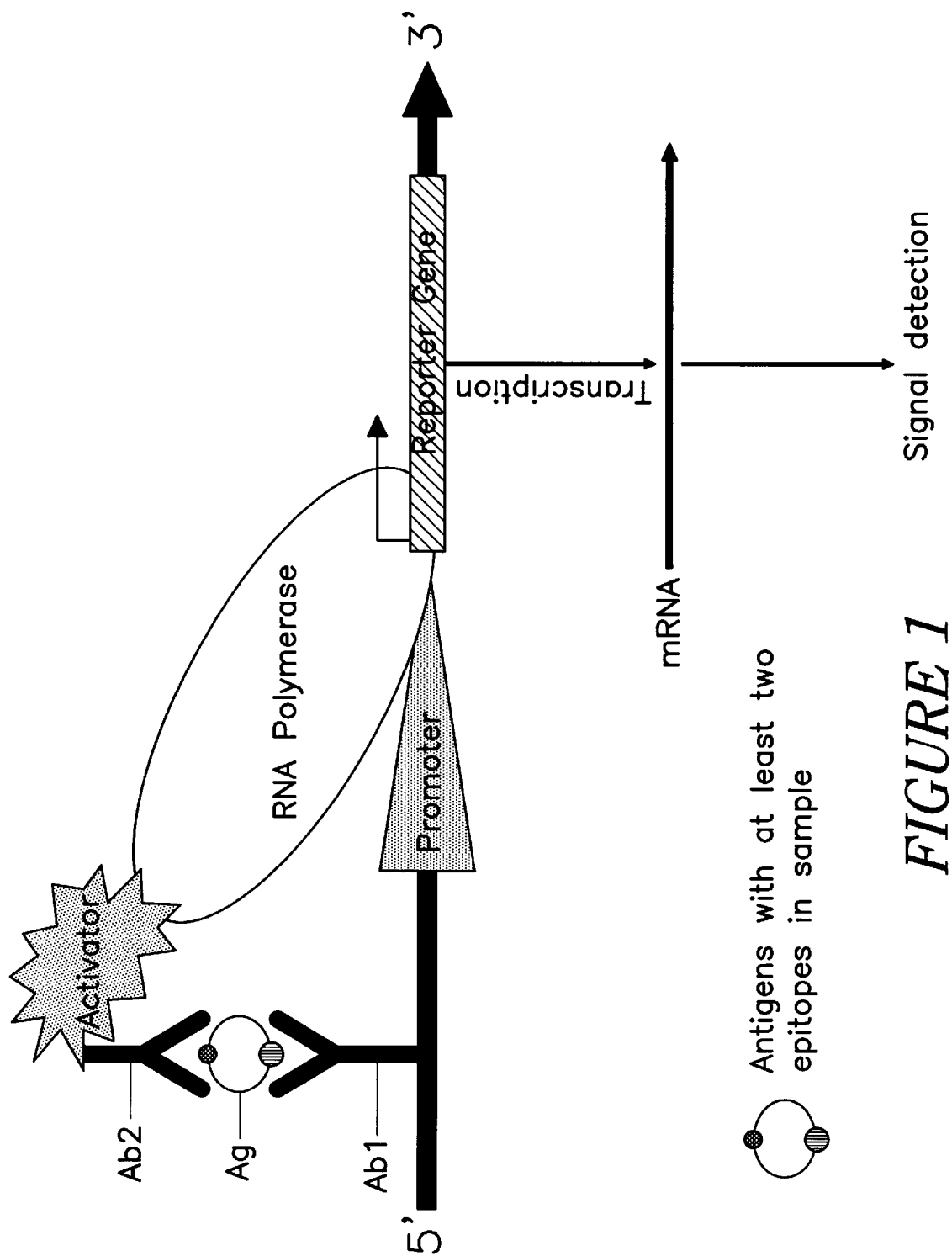
FIG. 1 is a schematic of an assay configuration according to this invention.

When the analyte is bound to the capturing agent and to the activator complex, the analyte typically serves as linker between the activator and the reporter construct, as illustrated in FIG. 1. As shown in FIG. 1, the analyte can be antigen, and the capturing agent and the activator complex each can be a binding moiety selected from the group of an entire antibody, a variable binding domain of an antibody, or at least a binding domain of the receptor, or a combination thereof, resulting in a specifically, but noncompetitively recognition of the antigen. By noncompetitively recognizing the antigen, it is meant that the analyte recognizing region, such as antibody or variable binding domains of the antibody of the activator complex, do not interfere with the binding of the capturing agent to the analyte. In one preferred embodiment of this invention, the analyte is a protein or peptide and the capturing agent and the analyte recognizing region are antibody, as shown in FIG. 1.

Figure 2:
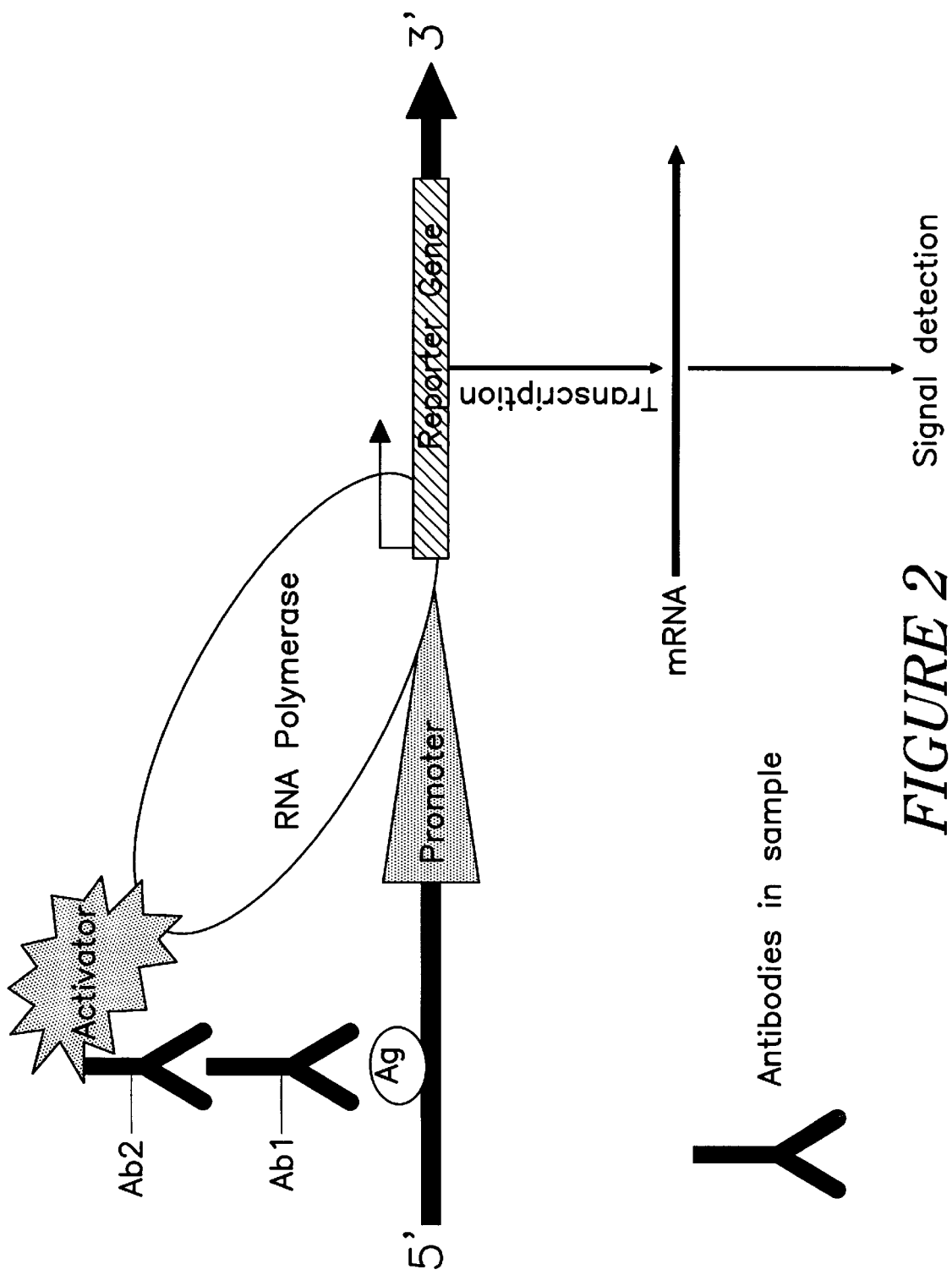
FIG. 2 is a schematic of another assay configuration according to this invention.

In another preferred embodiment, the analyte can be antibody, as shown in FIG. 2. FIG. 2 shows that the capturing agent in this embodiment is preferably antigen or a receptor capable of specifically recognizing the antibody. In another aspect of this invention, the assay can serve as an in vitro screening assay to identify molecules designed either to promote or to interfere with the interaction of two proteins, as illustrated in FIG. 3, wherein antibody can be used as a capturing agent in the DNA construct.

Figure 3:
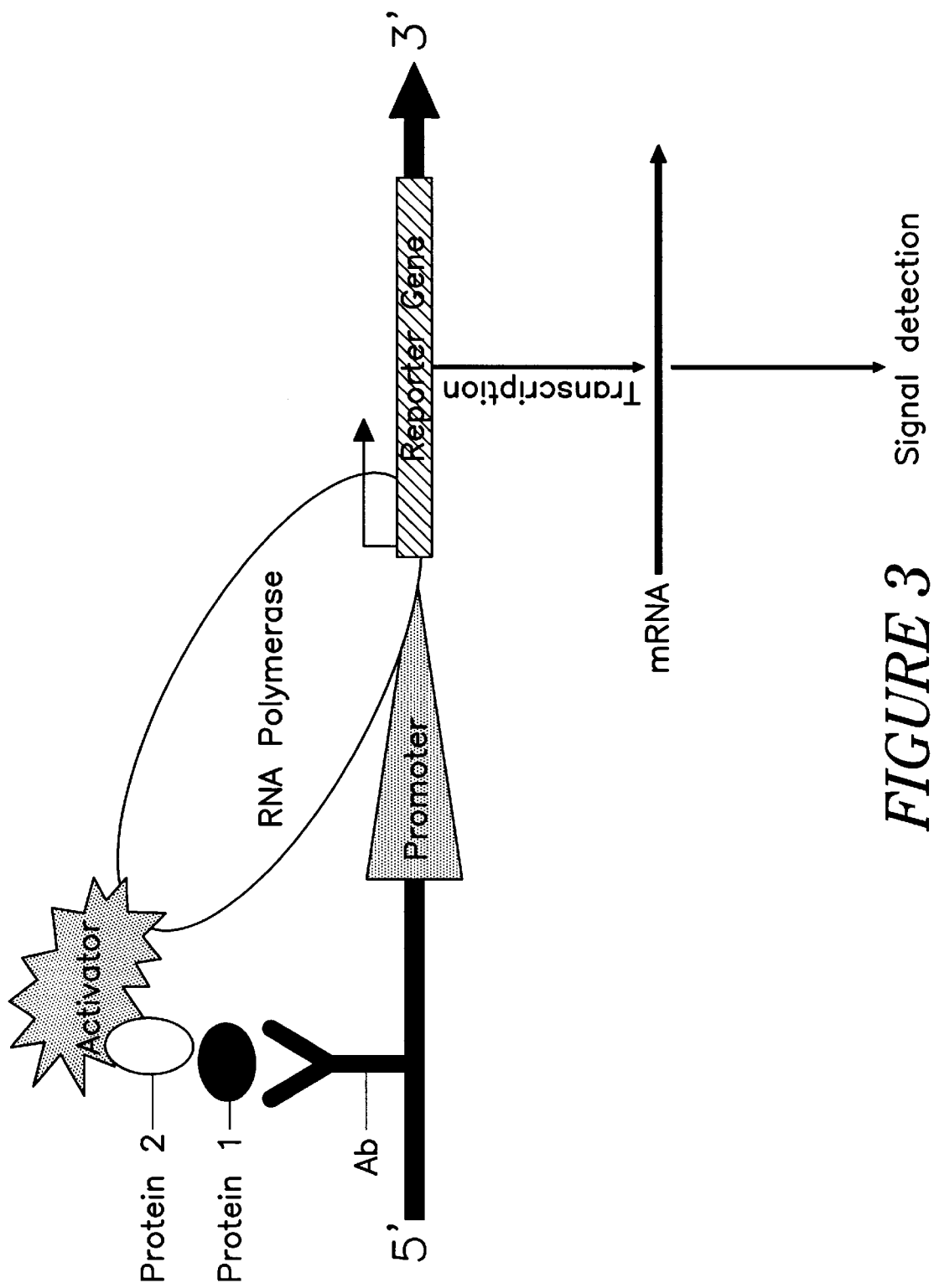
FIG. 3 is a schematic of yet another assay configuration according to the present invention.

The scenario depicted in FIG. 3 can be used, for example, in a drug screening assay, where two proteins or molecules can be expressed and purified. A first protein or molecule is affixed to the DNA construct according to this invention (i.e, a promoter, reporter, and the first protein or antibody to the first protein). Antibodies to the second protein or molecule or the second protein or molecule itself that is known to interact with the first protein or molecule is affixed to the activator to form an activator complex. Where antibodies to the first protein are affixed to the DNA construct and antibodies to the second protein are affixed to the activator complex. The reagents are mixed in the presence of the first protein or molecule and the second protein or molecule. Samples of drug or molecules to interfere, for example, with the association to the first protein and the second protein are then tested for their ability to interfere with or to promote activation of transcription. The target proteins do not need to be purified if an antibody against either one of the proteins can be generated. The other protein can be then combined with an activator. The presence of target protein capable of effecting transcription can be assessed in the system with relative ease.

Figure 4:
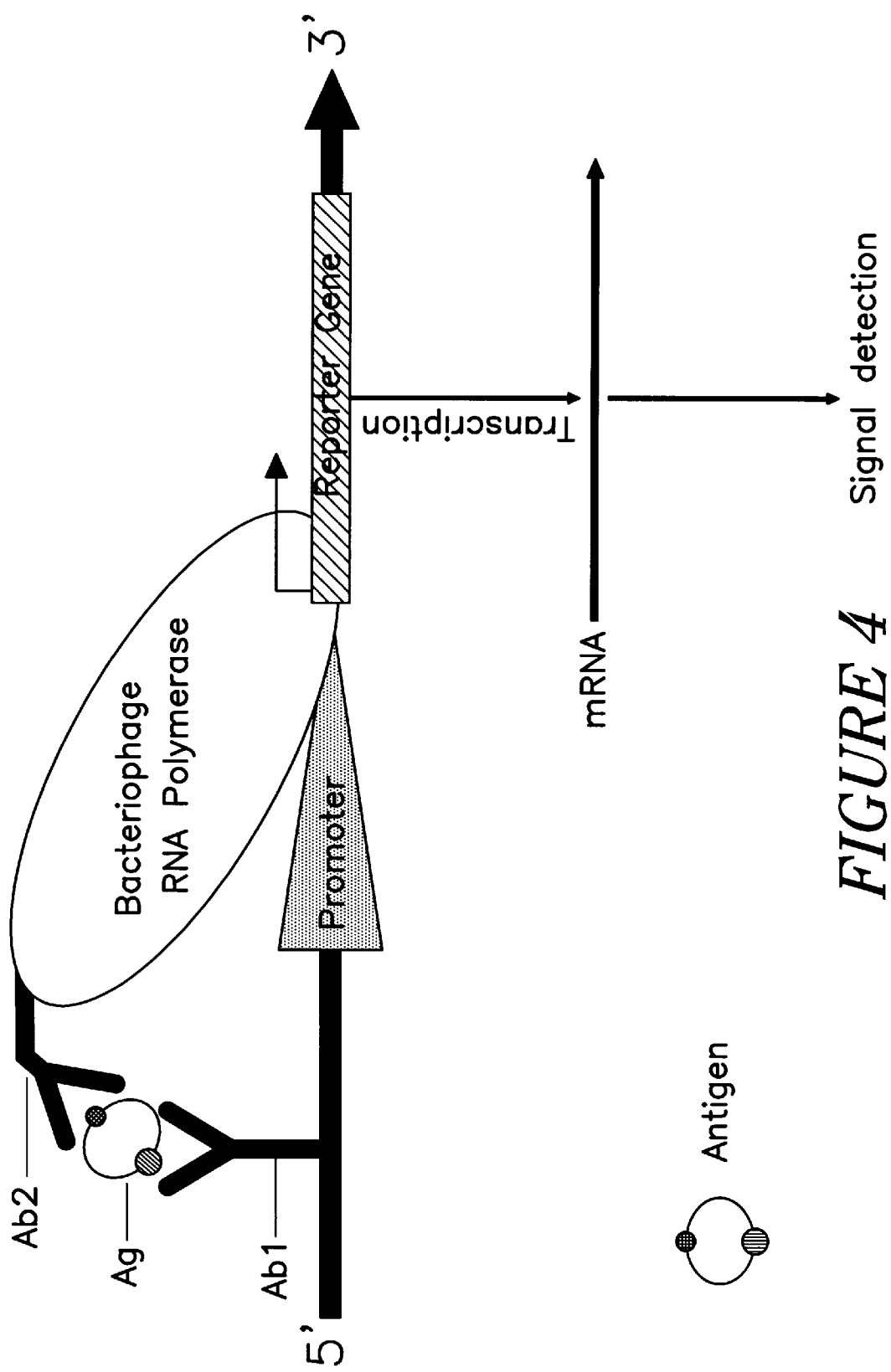
FIG. 4 is a schematic of yet a further assay configuration according to the present invention.

A further assay scenario is illustrated in FIG. 4 which employs a phage in vitro transcription system. In this system, a prokaryotic promoter, such as a T3 promoter, a T7 promoter, or an SP6 promoter (commercially available from Promega, Stratagene, and the like), includes specific nucleotide sequences which enable specific binding of the respective RNA polymerase. It is known that such promoters typically contain different domains that are responsible for different phases of transcription, such as polymerase binding, transcription initiation, etc. See e.g., Sousa R., et al., *J MoL Biol,* 224:319–334 (1992); Weston B. F., et al., *J MoL Biol.,* 272:21–30 (1997); Ikeda R.A., et al., *Proc. Natl. Acad. Sci.,* 83:3614–3618 (1986); and Schick C. et al., Biochemistry, 34:666–672 (1995). It is believed that when a mutation is introduced into the region responsible for polymerase binding, the polymerase fails to bind to the promoter such that transcription does not occur. See, e., Ikeda R. A. et al., Biochemistry, 31:9073–9080 (1992); and Osumi-Davis P. A. et al., J Mol. Biol., 237:5–19 (1994). However, if the polymerase can be captured close enough to the promoter, preferably without polymerase binding activity, transcription should occur because the other domains are still intact. Thus, in this scenario, elimination of polymerase binding activity by introducing at least one mutation in that domain (either by deletion or replacement of at least one nucleotide), the polymerase itself can then serve as part of the activator complex. In this system, Antibody 2 is linked to a bacteriophage RNA polymerase by conventional conjugation techniques. Therefore, when the activator complex is captured onto the promoter by analyte/analyte recognizing region interaction, transcription can still be achieved. Because phage systems (e.g, T3, T7, and SP6) are typically efficient, the sensitivity of the assay can be improved.

According to the present invention, the DNA can be any isolated DNA fragment that includes a reporter, such as a gene or a portion of a gene, under the control of an transcriptional activator responsive promoter, a transcriptional activator responsive promoter capable of associating with the transcriptional machinery and directing transcription of the reporter, and a capturing agent bound to the DNA.

In one embodiment according to the present invention, the promoter can be any promoter capable of associating with the transcriptional machinery in the assay and capable of directing transcription of the reporter DNA. The promoter used for reporter expression is non-constitutive and is transcriptional activator-responsive. A strong promoter with little or no background expression of the promoter will increase the sensitivity of the assay. A preferred promoter is one that is responsive to transcriptional activators in the assay and is capable of directing transcription of the promoter. A variety of promoters can be used in this assay. For example, gal (Fields S and Song O-K, supra), Elb minimal (available in Clontech's Palo Alto, Calif.) mammalian two hybrid system), the yeast promoter PHO5 (Gaudreau L. et al. Cell. 89:55–62, 1997) and E4 (Tantin, D. et al., supra) promoters can be used as well as prokaryotic promoters such as placOR$_R$2-62 (Dove SL et al. supra), including bacteriophage promoters known in the art, such as T3, T7, and SP6 to name a few. The promoters selected are capable of being regulated by the transcriptional activation domain selected in the assay. That is, the promoters are transcriptional activation domain responsive. The promoters do not initiate transcription unless they interact with a transcriptional activation domain. While the structure of the promoter can vary, the promoter must be able to activate transcription of the reporter when the activator complex is bound to analyte.

The activator and promoter are selected based on their ability to cooperate to activate transcription in the presence of transcriptional machinery. Eukaryotic and prokaryotic gene expression is regulated by a variety of transcriptional factors (Ptashne, M. and Gann A., Nature 386(6625):569–77, 1997). In general, a typical gene contains a promoter and a regulatory site for the binding of its specific transcriptional factor. This complex interacts with RNA polymerase to initiate or repress gene transcription. Gene expression requires the presence of transcriptional factors. While many transcriptional factors have been identified, they share some common features. For example, eukaryotic transcriptional factors generally contain an activation domain, to interact with transcription machinery, and a DNA binding domain. Transcriptional factors have the ability to bind to a regulatory site either through a specific DNA binding domain or by interacting with another DNA binding protein. The specificity of gene regulation is often controlled by the DNA binding properties of the transcriptional factors. That is, transcription is activated when the transcriptional activators bind to specific DNA binding sites on the DNA. In addition, the functions of the transcriptional factors is distance-, orientation-, and copy number-independent (see reviews by Blau J. et al. 1996. Mol. and Cell Biol. 16(5):2044–55; Farmer G. et al. 1996. Mol. and Cell Biol. 16(8):4295–340; and Hippenmeyer P. and Pegg LE. 1995. Current Opinion in Biotech. 6:548–52).

One of the more widely studied eukaryotic gene regulation system is the galactose regulon of yeast (Johnston AS et al. 1988. Cell 50(1):143–6 and Lohr, D. et al. 1995. FASEB J 9:777–87) that controls the expression of enzymes required for galactose metabolism. In the absence of galactose, the transcriptional activator, gal4, is inhibited by binding with another protein gal80. In an in vivo system, galactose can release gal4 protein from gal80. The gal4 protein is then free to bind to upstream activation sequences ($UAS^G$) to initiate gene expression. The gal4 protein contains a DNA binding domain (amino acids 1–147), and a major activation domain (amino acid 768–881, Horikoshi M. et al. 1988. Cell 54:665–9). When the DNA binding domain is replaced with another DNA binding protein (lexA, Chasman DI and Kornberg RD. 1990. Mol. and Cell. Biol. 10(6):2916–23), gal4 activates trascription from promoters with lexa binding sites. In addition, fusion of the gal4 DNA binding domain to the virus transcriptional factor, VP16, resulted in activation of the gal promoter (Fields S. and Song O-K. 1989. Nature 340:245–6).

Purified gal4, gal4 derivatives and gal4-VP16 fusion protein have been prepared successfully (Chasman et al., supra).

Protein-protein interactions can be assessed in vivo using a yeast two-hybrid system (Fields S and Song O-K. supra and Fields S and Stemglanz R. 1994. TIG. 10(8):286–92). The system takes advantages of the separate DNA binding and major activation domain of gal4. By fusing two different proteins (X and Y) into either the activation domain or the DNA binding domain, the specific interactions between the two proteins were identified using reporter gene expression under the control of a gal promoter. Transient positioning of the activation domain with polymerase II was enough to activate transcription. (Estojak J. et al. 1995. Mol. Cell Biol. 15(10):5820–9). The system has been modified to include a different DNA binding domain (lexA) or a different activation domain (VP16), and has been shown to work in other eukaryotic systems (see Feilds S. and Sternglanz R. 1994. TIG 10(8):286–92 and Phizicky Em and Fields S. 1995. MicrobioL Rev. 59:94–123), indicating that the transcriptional machinery is highly conserved among eukaryotic species. A similar system has been developed in E. coli that permits further study of protein-protein interactions (Dove SL et al. Nature 386:627–30, 1997).

Eukaryotic and prokaryotic transcriptional machinery are available commercially or can be prepared, for example, from cell lysates. For eukaryotic cells the cell lysates generally include at least a nuclear lysate isolated from cells. The assays of this invention produce RNA from the reporter DNA and the in vitro transcription machinery, according to this invention, preferably comprises nuclear lysate from cells capable of transcription, rNTPs (ribonucleotides) capable of being incorporated into an elongating RNA strand and a suitable buffer system, such as buffers that are commercially available for in vitro transcription (for example, available in the literature or commercially available from suppliers such as Stratagene, Invitrogen, Promega, and the like). Defined components of transcriptional machinery can also be purified separately, or in whole, such as holoenzyme preparations that are known in the art.

In accordance with the present invention, the reporter can include all or a portion of a variety of reporter DNA sequences known in the art. Preferably, the reporter is a gene or a portion of a gene or a synthetic DNA fragment that can be transcribed. The RNA transcribed from the reporter can be detected either as RNA or through translation of the RNA into protein. Where the RNA is translated into protein, preferably the protein is part of a reporter system. Examples of reporter systems are well known in the field of molecular biology and include, but are not limited to, luciferase (from Promega, Madison, Wis.). Other suitable reporters known and used in the art include β-galactosidase, horseradish peroxidase and alkaline phosphatase. These reporter sequences and DNA fragments are available from commercial sources and the DNA and protein sequences are available from GenBank, for example. The signal generated by the translated reporter can be correlated with the number of MRNA templates and mapped as a function of the amount of analyte in a sample to provide standard curves that relate a particular level of signal to a particular amount of analyte. Such methods are well known in the art of assay design. The degree of transcription (MRNA concentration produced per given amount of time) is dependent on the number of constructs containing the activator captured through the analyte-mediated capturing agent activator complex interaction. The more analyte present in the sample, the more activator can be captured, resulting in a higher degree of transcription.

The assay of the present invention is preferably performed by adding a volume of sample suspected of containing analyte to the DNA fragment, comprising the capturing agent, and to the activator complex. The reaction vessel also includes reagents sufficient to support transcription. Where the end product of the assay is the product of translation, then the reaction vessel also includes reagents sufficient to support translation, such as a bacterial lysate or reticulocyte lysate. Where the end product of the assay is the product of translation, in vitro gene expression is observed through the detection of a signal that complements the reporter expression. That is, the reporter molecules known in the art and contemplated for use in this invention include known reporter protein and substrate. Typically the reporter protein acts on the substrate to generate a signal, such as a precipitate, a color change, light (i.e., luminescence) or the like. For example, where the reporter protein is luciferase, the substrate is luciferin and the production of light is measured using a luminometer (e.g., from Promega, Madison, Wis.)

The components of this invention preferably meet the following requirements. First, the capture agent must be in a proximity to the promoter such that the binding of an activator complex through the association of an analyte will activate transcription from the promoter that can activate the transcription when an activator is captured in the assay. In one embodiment, the distance between the capture agent and the promoter on the DNA fragment is at least about 20 base pairs (bp) and preferably less than 500 base pairs. The distance between the capture agent and the promoter can be optimized by positioning the promoter adjacent to the reporter and testing for transcriptional activation as a function of the distance between the capture agent and the promoter (see for example assays of Fields S and Song O-K. 1989. *Nature* 340:245–6 and Fields S and Stemglanz R. 1994. *TIG.* 10(8):286–92 and the assays of Tantin D. et al, supra). The capture agent can be ssociated with the DNA fragment by any of a variety of methods known in the art ncluding, but not limited to, the use of heterobifinctional cross-linking reagents and ther methods disclosed for example by Hermanson, G. (Bioconjugate Techniques. 1996. Academic Press, N.Y.).

Second, the reporter must produce a transcription product that can be detected either as RNA or as a product of translation when the activator is positioned adjacent to the promoter. The activator should be selected as an activator that can activate expression of a reporter construct from a particular promoter in the presence of transcriptional machinery.

Third, the analyte-binding region of the activator complex, whether antibody, variable antibody domains, a receptor, or the like, should be specific to the analyte and not adversely interfere with the recognition of the capturing agent with the analyte. In addition, the activator portion of the activator complex must be functional and preferably only functions when the analyte recognition region is bound to analyte.

Fourth, the reaction vessel should contain the necessary components to facilitate in vitro transcription and can include the necessary components to facilitate translation. Preferably the components in the reaction vessel lack endogenous factors that initiate gene expression from the DNA construct and produce a significant background. Assaying the background level in a particular assay can be performed by running the assay in the absence of analyte or in the presence of a nonspecific analyte (such as antibody in a serum sample lacking analyte).

Unlike commercially available bacteriophage-derived RNA polymerases, purified eukaryotic transcription machinery is not commercially available; however, the machinery can be purified in the laboratory using a variety of methods known in the art. In vitro gene expression outside of a cell requires nuclear extracts to provide all of the factors necessary for transcription . Nuclear extracts for eukaryotic transcription have been isolated from HeLa cells and Drosophila embryos and these are commercial available. A cell free in vitro transcription system has also been developed using yeast nuclear extract (Woontner M and Jaehning J. 1990. *J BioL Chem.* 265(16):8979–82, Flanagan PM et al. 1990. *J. Biol. Chem.* 265(19):11105–7, Lue NF and Komberg RD. 1987. *Proc. Natl. Acad. Sci. USA* 84:8839043, Ohashi Yet al. 1994. *Mol. and Cell. Biol.* 14(4):2731–9 and Lue NF et al. 1991. *Methods Enzymol.* 194:545–50). Transcriptional factor-directed expression, such as Gal4-directed expression, was observed in in vitro systems using both yeast and HeLa nuclear extract (Lin Y-S and Green MR. 1991. *Cell.* 64:971–81 and Lin Y-S et al. 1988. *Cell* 54:659–64). In vitro transcription and translation have been successfully coupled in bacteriophage systems, and technologies are available for coupled eukaryotic transcription/translation system (Torik AY and Wim JM, supra and Leibowitz MJ et al. 1991. *Methods Enzymol.* 194:536–44).

Figure 5A:
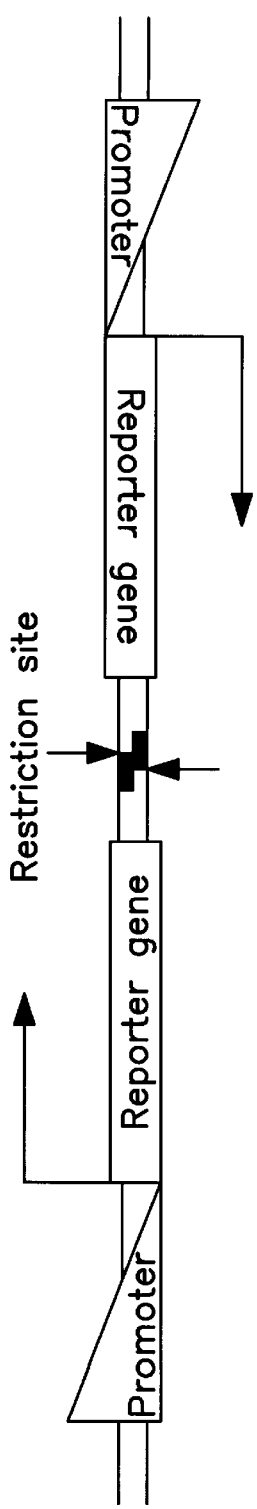
FIG. 5A is a diagram of a preferred DNA construct for use in a detection assay according to this invention.

The capturing agent can be affixed to the DNA construct using a variety of methods including heterobifunctional cross-linkers that chemically link the capturing agent to one or both end(s) of the reporter expression construct, as described above. Using these methods, both ends of the DNA molecule will be labeled. This could create a dilution problem since without additional modification, one-half of the capturing molecules would not be available for reporter gene activation. However, one way to overcome this problem is by creating a duplex reporter system such as that provided in FIG. 5A. As shown in FIG. 5A, the DNA construct can be engineered to contain two copies of reporter constructs at different orientations. In one embodiment, the reporter genes are separated by a restriction site. After both ends of the construct are conjugated with capturing agent, the DNA construct can be cleaved into two functional constructs with only one end (upstream of promoter) labeled. In another embodiment (not shown), the construct is not separated, particularly where the capturing agent on the DNA fragment is provided in excess relative to the amount of analyte present. Alternatively, a strong terminator can be introduced into the 3' end of each reporter gene to prevent the polymerase from running into the other copy of reporter gene positioned in the opposite orientation.

In another method for linking the capturing agent to the DNA construct, the upstream sequences (upstream of the promoter) may be synthesized as oligonucleotides with one or more bases labeled with linker chemicals such as biotin are incorporated into the oligonucleotide. The DNA construct is formed by ligation or PCR. The capturing agent can be associated to the DNA fragment using an avidin labeled protein such as, for example, an avidin labeled antibody or an avidin labeled protein, and the like.

The position and number of sites for associating the capturing agent to the DNA construct can vary to optimize a particular reporter/ activator complex/ promoter/ capturing agent system.

The activator portion of the activator complex can include an activating region from a variety of transcriptional factor including, but not limited to gal4, VP 16, ZEBRA (Chi T and Carey, M. supra), λcI-CTD (prokaryotic system, Dove SL et al., supra), other transcription activators provided by Lin Y-S, (*Cell*, 54:659–64, 1988 and by Chasman DI and Kornberg RD. 1990. *Mol. and Cell. Biol.* 10(6):2916–23), and article activators such as synthesized small peptides. In one embodiment the activator portion of the activator complex is gal4 or its derivatives (Lin Y-S, supra and Chasman, DA and Kornberg, supra). A variety of activators are suitable for use in this system if the activator can be bound to an analyte recognition region, such as a receptor, an antibody or a fragment of an antibody and if the activator complex can activate transcription from a selected promoter. Technologies are available for stable conjugation of an analyte recognition molecule, such as an antibody with an activator protein without loosing the activity of that protein (see for example Hermanson GT, Bioconjugate Techniques, supra). One or more analyte recognition molecules can be bound to a given activator as long as the ability of the activator to activate transcription from the reporter gene is not inhibited.

An assay in accordance with the present invention has a number of benefits as compared with other assays. For example, the assay is self contained within a single tube. Only the sample or dilutions of the sample are added. In a preferred embodiment, no coating, washing and separate additions of different reagents are required. The assay is fast and can be completed within less than one hour to about 4 hours, preferably within about 2 hours and more preferably within about 30 minutes to about 2 hours. Since signal is generated only if the activator complex is brought into the contact with RNA polymerase by two specific reactions between the capturing agent and the analyte and between the activator complex and analyte, the background, if there is any, will be totally independent from the specific binding of the capturing agent and activator complex to the analyte.

In addition, the assay is sensitive. The efficiency of gene expression is dependent on the affinity and strength of the activator for its DNA binding site (regulatory site). Where antibody and antigen are used, the assay gains the benefit of the specificity of the antigen-antibody complex that is formed. Moreover, transcription is initiated continuously after the capture agent, analyte and activator complex associate and signal is generated even if the capture agent, analyte and activator complex disassociate. The longer the association, the more mRNA will be produced, resulting in enhanced signal through an efficient signal amplification process. Unlike most competition type assays, the concentrations of both the activator complex and the DNA construct can be added in great excess, driving the specific analyte-recognition reactions towards the direction of complex formation even in the presence of trace amount of analyte in sample.

The assay is readily adaptable to a variety of automation procedures and is useful for detecting a wide variety of analytes, whether antibody or antigen as long as the analyte has at least two sites: an activator complex binding site and a capturing agent binding site. Further, there is no strict requirement for antibody/antigen or ligand/receptor affinity. Even the transient positioning of analyte with the activator complex will initiate transcription. Therefore, antibody or receptors used as capture agent or as activator complex with lower affinities (such as affinities weaker than $10^{-8}$, for example), can still generate signal as long as they pecifically bind analyte.

The following Examples are presented for the purposes of illustrating the present invention and it is to be recognized that there are a variety of alternative echniques and procedures available to those of skill in the art which would imilarly permit one to successfully practice the invention.

EXAMPLE 1

Sensitivity of Assay to RNase

The presence of RNase in a sample was evaluated. This is important for many samples capable of being screened in the present invention, such as a serum sample, that could degrade the mRNA templates and reduce the sensitivity of the assay. In this Example, RNase A, RNase B and RNase C (all available from Sigma, St. Louis, Mo.) were titrated with varying dilutions of luciferase mRNA. Dilutions of RNase were prepared from $10^{-6}$ to $10^{-20}$ mol using ddH$_2$O. Individual RNase reactions were prepared as follows: 8.5 μl of 1.221 mM MgSO$_4$, 0.5 μl RNA (10 ng/μl), and 1 μl of RNase dilution. The samples were incubated at 30° C. for about 24 hrs. Following incubation 1.5 μl of the sample was added into 7.5 μl of in vitro translation mix (rabbit reticulocyte lysate, amino acids, KCI and RNasin as provided in an in vitro translation kit available from Promega, Madison Wis.) and incubated at 30° C. for 1 hour. An aliquot of 2 μl of each reaction were mixed with 50 μl of luciferase substrate (per kit) and results were read using a luminometer within 1 min. of sample addition.

Results indicated that RNase concentrations of $10^{-9}$ mol or lower had little effect on RNA stability. For RNase A, the molecular weight is about 15 kD, converting this to weight concentration the cut off for RNase addition is about 15 pg/ml. In the presence of RNase inhibitor, RNase concentrations of about $10^{-5}$ to about $10^6$ mol or less had little effect on RNA stability. These results indicate that the RNase concentration in most of biological samples is substantially lower than the tested limit, therefore, the immunoassay will not be sensitive to RNase present in samples.

EXAMPLE 2

Dilution of Transcription and Translation Components do not Lower Assay Sensitivity Although the dilution can be compensated by using more concentrated extract or lysate, the effect of dilution on the efficiency of in vitro translation was tested since batches of lysate can vary. This Example examines dilution of both transcription and translation components after the sample is added into the reaction.

Commercially available eukaryotic cell lysate (from Promega) was evaluated to determine whether it could be diluted under the ranges required for the assay of this invention and still generate a signal. The following experiment was performed. A cocktail containing 1 $\mu$l of a 1 mM amino acid mix, 0.7 $\mu$l of 2.5M KCl, 0.5 $\mu$l of 40U/$\mu$l RNasin, 0.5 $\mu$l of 100 ng/$\mu$l Luciferase RNA, 5.8 $\mu$l $H_2O$ total volume of 8.5 $\mu$l was prepared. Rabbit reticulocyte lysate was diluted in serial two fold dilutions out to a 64 fold dilution using 1.221 mM $MgSO_4$. 16.5 $\mu$l of the dilution was added to the cocktail. An aliquot of 2 $\mu$l of the reaction was added to 50 $\mu$l luciferase substrate and results were read on a luminometer. Results indicated that a 32 fold dilution was still able to generate a detectable signal.

EXAMPLE 3

Paration of DNA Construct

The gene encoding luciferase was obtained from the Promega pGL3 vector using Xbal and HindIII. The luciferase gene was purified by gel electrophoresis. Two adapters were prepared to convert Xba I into BamHI using adapter sequences (referred to herein as an "X/B adapter"):
5'-CTAGAGGCGCGGGCCGGAAAAAAAA AAAAAAAAAAAAAAAAAAAAAAG CGCGGCG-3'(SEQ ID:1), and
5'-GATCCGCCGCGCTTTTTTTTTTT TTTTTTTTTTTTTTTTCCGGCCC GCGCCT-3' (SEQ ID:2)

Two adapters were used to invert a Hind III restriction site to EcoRI using an H/E adapter sequences (referred to herein as an "H/E adaptor"):
5'-AATTCTTCGCCGGATCTTTGTGAAG GAACCATT-TAGGTGACACTATATCC GTCGACTCTAGAGGG-TATATAATGC GCCGCTCGAAGA-3'(SEQ ID:3) and
5'-AGCTTCTTCGAGCGGCGCATTATAT ACCCTCTA-GAGTCGACGGATATAGT GTCACCTAAATGGTTC-CTTCACAAA GATCCGGCGAAG-3'(SEQ ID:4).

A polyA tail was included in the X/B adapter and the H/E adapter was modified to include the Elb minimal promoter. The fragments were ligated using a conventional ligation technique. Restriction endonucleases EcoRI and Barn Hi were used to release a fragment containing the EIb minimal promoter, luciferase coding sequence and the 3' polyA tail. The fragment was isolated by gel electrophoresis.

The fragment was incorporated into a plasmid pB SK+ (Stratagene, LaJolla, Calif.) to create a dimer in a plasmid using EcoRI. Prior to the addition of the capturing agent on the DNA fragment, the DNA fragment was removed from the plasmid using EcoRI. The luciferase dimer was then purified. The 5' phosphate on the DNA fragment was converted to either an amine or an SH group using a chemical linker such as 1-Ethyl-3-(3-Dimethylaminopropyl) carbodiimide (EDC, Pierce Chemicals, Rockford, Ill.).

An antibody or protein was chemically conjugated to the DNA using the procedures of Hermanson (supra). The fragment was isolated and the conjugated DNA was cut with BamHI to generate two 5' labeled fragments.

EXAMPLE 4

Activator Complex Production

An expression vector encoding the GAL4-$\lambda$VP$_2$ described by Ohasi Y. (supra) was transformed into E. coli XA90. Bacteria were grown at 37° C in Luria broth to an $A_{600}$ of 0.5, induced with 1 mM IPTC and grown for an additional 3 h at 37° C. The cells were harvested and lysed by sonication in buffer A containing 0.2M NaCl (buffer A was 20 mM HEPES, pH 7.6, 50 mM 2-mercaptoethanol, 10 $\mu$M $ZnCl_2$, 1 mM phenylmethylsulfonylfluoride, 10 $\mu$g of pepstatin per ml, and 10 $\mu$g of leupeptin per ml). The lysates were centrifuged to remove the insoluble material. Polyethyleneimine-HCl, pH 7.5 was added dropwise to the supernatant to a final concentration of about 0.25%. After the mixture had been stirred for 10 min., the precipitate was collected by centrifugation. The pellet was dissolved in 50 ml of buffer A containing 0.75 M NaCl and resuspended by homogenization. The mixture was centrifuged again, and the GAL4-$\lambda$VP$_2$ was present in the supernatant. Solid ammonium sulfate is added slowly to 35% saturation. After the mixture had been stirred for min. on ice, the precipitate containing the GAL4-$\lambda$VP$_2$ was collected by centrifugation. The pellets were dissolved in 20 ml of buffer A and the mixture was applied to 5 ml heparin-Sepharose CL 6B columns (commercially available from Pharmacia) equilibrated with buffer A containing 0.2M NaCl. The column was washed with buffer A containing 0.2M NaCl and developed with buffer A containing 0.6M NaCl. The peak fractions were identified by coomassie blue staining of SDS-PAGE gels. The NaCl concentration of the pooled peak was measured by conductivity and adjusted to 2.5M, and the mixture was applied to 4 ml phenyl Sepharose column (from Pharmacia) equilibrated in buffer A containing 2.5M NaCl. After being washed with buffer A containing 2.5 M NaC, the column was developed with three successive steps of buffer A containing 1.5, 0.6 and 0M NaCl, respectively. GAL4-$\lambda$VP$_2$ was eluted predominantly with buffer A.

A capture antibody was dissolved in buffer B containing 0.1M NaCl (buffer B was 0.1M sodium phosphate, pH 7.4) at the concentration of 4 mg/ml; 2-iminothiolane in borate buffer at the concentration of 1 mg/ml; and SPDP in ethanol at the concentration of 80 mM. GAL4-$\lambda$VP$_2$ was exchanged into buffer B to a final concentration of the activator of 1 mg/ml. The capture antibody was combined with 2-iminothiolane at the molar ratio of about 1:40. The reaction was incubated at room temperature for about 1 hour. The activator was combined with SPDP at 2.5:1 molar ratio and incubated at room temperature for about 30 minutes. The reaction was passed through a PD-10 column. The protein concentration of the PD-10 column fractions was measured at $A_{260}$. The activator and the capture antibody were combined at a 40:1 molar ratio. The conjugated antibody can purified from free antibody using any one of a variety of conventional purification techniques such as HPLC, gel filtration, dialysis and/or molecular weight cut-off filter. An SDS-PAGE gel was run to confirm the purity and conjugation of the conjugated antibody. The resulting DNA construct typically has construct as shown in FIG. 5A.

EXAMPLE 5

Capture Antibody Conjugation to DNA

The dimer construct according to FIG. 5A was cut with EcoRI and a resulting 3.6 kB fragment was purified by gel electrophoresis and eluted. Activated DNA was prepared by adding 7.5 $\mu$l (57–115.5 $\mu$g) of the DNA fragment into a microcentrifuge tube containing 1.25 mg Carbodimide EDC (Pierce). 5 $\mu$l of 0.25M cystamine in 0.1M imidazole, pH 8.0 was added to the reaction and mixed by vortexing. The sample was spun for 5 minutes at 16,000 rpm using a microcentrifuge. 20 μl of 0.1M imidazole, pH 6.0 was added to the tube, mixed and reacted for 30 minutes at room temperature. 20 μl of 0.1M DTT was added to the tube to reduce cystamine and to create thiol groups at the 5' ends of the DNA. The DNA was purified by gel filtration using Sephadex G25 column (available from Pierce).

SPDP activated antibodies were prepared by dissolving the antibody in 0.1M sodium phosphate containing 0.15M NaCl and 10 mM EDTA, pH 7.5. The final concentration was adjusted to 1 mg/ml. SPDP was dissolved in DMF to a concentration of 3 mg/ml. 3 μl of the SPDP solution was added to 1 ml of antibody solution and mixed until there is complete dissolution. The reaction was allowed to continue for 30 minutes at room temperature. Excess cross-linkers were removed by gel filtration using Sephadex G25 columns.

Figure 5B:
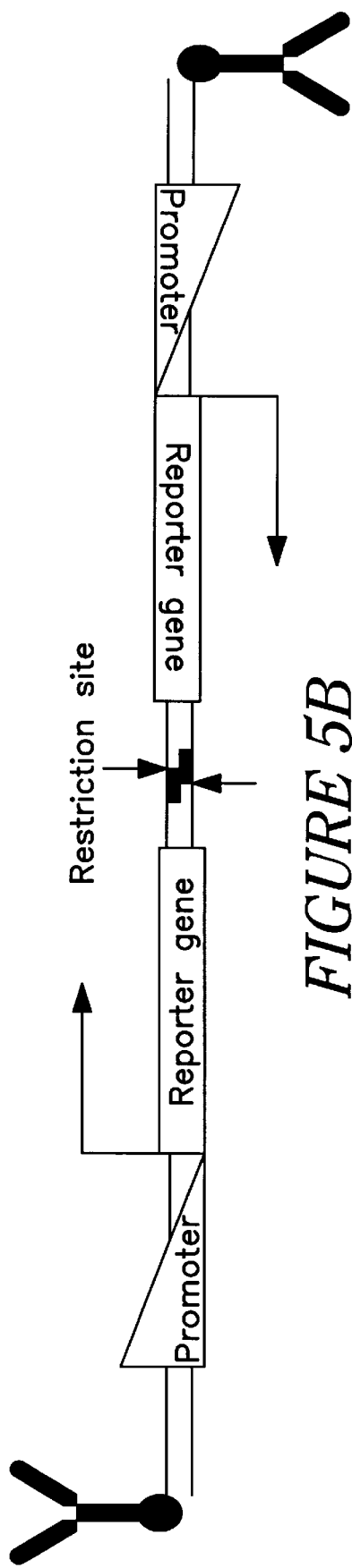
FIG. 5B is a diagram of a preferred DNA-capturing agent conjugate configuration according to this invention.

Activated DNA was conjugated to activated antibodies by mixing 100 μg of activated DNA with 75 μg of activated antibody (molar ratio of DNA to antibody was about 1:1 00) and incubated at room temperature for about 1 hour. The reaction was incubated at 4° C. overnight. The conjugated DNA was purified using an S-300 gel filtration column. The resulting activated antibody-DNA conjugate is depicted in FIG. 5B, although as indicated, the DNA may also be conjugated to an activated antigen.

EXAMPLE 6

Assay Testing for Translation Product

The conjugate including a DNA fragment and an activated antibody were prepared as described above. In this Example, the conjugate was prepared using Gal4 chemically conjugated to an antibody recognizing a second epitope to the first protein where the antibody used in the DNA construct and antibody used in the activator complex do not compete for binding sites. The DNA fragment, the activator complex, a nuclear extract from eukaryotic cells and a rabbit reticulocyte lysate were combined in a reaction vessel with a total volume of about 20 μl to about 50 μl. The concentrations of these components were added within the range of a standard in vitro translation assay known in the art. The DNA fragment was preferably added in the range of about 5 ng/μl to about 50 ng/μl and the activator complex was preferably added at a concentration of about 2 ng/μl to about 100 ng/μl. The reaction vessel was incubated preferably at about 30° C. for about 1 hour to about 2 hours. Luciferin was added to the sample according to standard assay concentrations (Promega luciferase assay system) and light was measured using a luminometer, as described by Promega. A standard curve was plotted using samples with known concentrations of the protein and the unknown amount of sample can be determined based on the standard curve.

Patents, patent applications, and documents disclosed herein are hereby incorporated by reference as if individually incorporated. It is to be understood that the above description is intended to be illustrative, and not restrictive. Various modifications and alterations of this invention will become apparent to those skilled in the art from the foregoing description without departing from the scope and the spirit of this invention, and it should be understood that this invention is not to be unduly limited to the illustrative embodiments set forth herein.

What is claimed is:

1. An in vitro method for detecting analyte in a sample comprising:
adding a sample to a sample reservoir, wherein the reservoir comprises:
(a) an isolated DNA fragment comprising a capturing agent linked to DNA, wherein the DNA comprises at least one promoter and at least one reporter DNA;
(b) reagents comprising those suitable for supporting transcription from a DNA fragment; and
(c) an activator complex comprising an activator and an analyte recognizing region;
incubating the sample in the reservoir for a time sufficient to generate transcription of the at least one reporter DNA to produce reporter RNA; and
detecting the presence of reporter RNA in the reservoir wherein the presence of reporter RNA indicates that the analyte is present in the sample.

2. The method of claim 1 wherein the reagents further comprise those suitable for supporting translation.

3. The method of claim 1 wherein detecting further comprises translating reporter RNA into protein and the sample reservoir further comprises reagents suitable for supporting translation of reporter RNA.

4. The method of claim 1 wherein the promoter is a prokaryotic promoter and the reagents are suitable for supporting transcription from prokaryotic DNA.

5. The method of claim 1 wherein the detecting step comprises detecting RNA produced from the reporter.

6. The method of claim 2 wherein detecting further comprises detecting protein produced from the RNA.

7. The method of claim 1 wherein the capturing agent comprises a moiety selected from the group consisting of an antibody, a variable binding domain of an antibody, a binding domain of an antibody receptor, or a combination thereof.

8. The method of claim 1 wherein the analyte recognition region comprises a moiety selected from the group consisting of an antibody, a variable binding domain of an antibody, a binding domain of an antibody receptor, or a combination thereof.

9. The method of claim 7 wherein the analyte comprises a peptide.

10. The method of claim 1 wherein the capturing agent comprises a peptide.

11. The method of claim 9 wherein the analyte comprises a peptide recognition moiety selected from the group consisting of an antibody, a variable binding domain of an antibody, a binding domain of an antibody receptor, or a combination thereof.

12. An in vitro kit for the detection of an analyte comprising:
reagents comprising those that are suitable for supporting transcription from a DNA fragment;
an isolated DNA fragment comprising a capturing agent linked to a DNA, wherein the DNA comprises at least one promoter and at least one reporter DNA;
an activator complex comprising an activator and an analyte recognition region; and
at least one reaction reservoir.

13. The in vitro kit of claim 12 wherein the reagents further comprise those that are suitable for supporting translation.

14. The in vitro kit of claim 12 wherein the reagents further comprise those that are suitable for supporting eukaryotic translation.

15. The in vitro kit of claim 12 wherein the reagents further comprise those that are suitable for supporting prokaryotic translation.

16. The in vitro kit of claim 12 wherein the DNA comprises two copies of a promoter linked to a reporter DNA, wherein one copy is oriented opposite the other copy.

17. The in vitro kit of claim 16 wherein one copy of the promoter linked to the reported DNA is separated from the other copy by a restriction endonuclease adaptor site.

18. The in vitro kit of claim 12 wherein the capturing agent and the promoter are separated by a distance in the range of about 20 base pairs to about 500 base pairs.

19. The in vitro kit of claim 12 wherein the capturing agent comprises a moiety selected from the group consisting of an antibody, a variable binding domain of an antibody, a binding domain of an antibody receptor, or a combination thereof.

20. The in vitro kit of claim 12 wherein the analyte recognition region comprises a moiety selected from the group consisting of an antibody, a variable binding domain of an antibody, a binding domain of an antibody receptor, or a combination thereof.

21. The in vitro kit of claim 12 wherein the capturing agent comprises a peptide.

22. An in vitro method for detecting analyte in a sample comprising:
adding a sample to a sample reservoir, wherein the reservoir comprises:

(a) an isolated DNA fragment comprising a capturing agent linked to DNA, wherein the DNA comprises at least one prokaryotic promoter and at least one reporter DNA;
(b) reagents comprising those suitable for supporting transcription from a DNA fragment; and
(c) a complex comprising an analyte recognizing region and a bacteriophage polymerase;

incubating the sample in the reservoir for a time sufficient to generate transcription of the at least one reporter DNA to produce reporter RNA; and detecting the presence of reporter RNA in the reservoir wherein the presence of reporter RNA indicates that analyte is present in the sample.

23. The method of claim 22 wherein the prokaryotic promoter comprises a nucleotide sequence having at least one point mutation deactivating bacteriophage polymerase binding activity of the prokaryotic promoter.

24. The method of claim 22 wherein the reagents further comprise those suitable for supporting translation.

25. The method of claim wherein detecting further comprises translating reporter RNA into protein and the sample reservoir further comprises reagents suitable for supporting translation of reporter RNA.

26. The method of claim 23 wherein the prokaryotic promoter is selected from the group consisting of a T3 promoter, a T7 promoter, and an SP6 promoter.

27. An in vitro kit for the detection of an analyte comprising:

reagents comprising those that are suitable for supporting transcription from a DNA fragment;

an isolated DNA fragment comprising a capturing agent linked to a DNA, wherein the DNA comprises at least one prokaryotic promoter and at least one reporter DNA;

a complex comprising an analyte recognition region and a bacteriophage polymerase; and at least one reaction reservoir.

28. The in vitro kit of claim 27 wherein the prokaryotic promoter comprises a nucleotide sequence having at least one point mutation deactivating bacteriophage polymerase binding activity of the prokaryotic promoter.

29. The in vitro kit of claim 28 wherein the reagents further comprise those that are suitable for supporting translation.

30. The in vitro kit of claim 28 wherein the capturing agent comprises a moiety selected from the group consisting of an antibody, a variable binding domain of an antibody, a binding domain of an antibody receptor, or a combination thereof.

31. The in vitro kit of claim 28 wherein the analyte recognition region comprises a moiety selected from the group consisting of an antibody, a variable binding domain of an antibody, a binding domain of an antibody receptor, or a combination thereof.

32. An in vitro method for detecting analyte in a sample comprising:

adding a sample to a sample reservoir, wherein the reservoir comprises:
(a) an isolated DNA fragment comprising a capturing agent cross-linked to DNA, wherein the DNA comprises at least one prokaryotic promoter and at least one reporter DNA;
(b) reagents comprising those suitable for supporting transcription from a DNA fragment; and
(c) a complex comprising an analyte recognizing region and a bacteriophage polymerase;

incubating the sample in the reservoir for a time sufficient to generate transcription of the at least one reporter DNA to produce reporter RNA; and detecting the presence of reporter RNA in the reservoir wherein the presence of reporter RNA indicates that analyte is present in the sample.

33. The method of claim 1 wherein the analyte is in solution.

34. The method of claim 22 wherein the analyte is in solution.

35. An in vitro method for detecting analyte in a sample comprising:

adding a sample to a sample reservoir, wherein the reservoir comprises:
(a) an isolated DNA fragment comprising a capturing agent linked to DNA, wherein the DNA comprises at least one eukaryotic promoter and at least one reporter DNA;
(b) reagents comprising those suitable for supporting transcription from a eukaryotic DNA fragment; and
(c) an activator complex comprising an activator and an analyte recognizing region;

incubating the sample in the reservoir for a time sufficient to generate transcription of the at least one reporter DNA to produce reporter RNA; and detecting the presence of reporter RNA in the reservoir wherein the presence of reporter RNA indicates that analyte is present in the sample.

36. An in vitro method for detecting analyte in a sample comprising:

adding a sample to a sample reservoir, wherein the reservoir comprises:
(a) an isolated DNA fragment comprising a capturing agent linked to DNA, wherein the capturing agent comprises a moiety selected from the group consisting of an antibody, a variable binding domain of an antibody, a binding domain of an antibody receptor, or a combination thereof, and wherein the DNA comprises at least one prokaryotic promoter and at least one reporter DNA;
(b) reagents comprising those suitable for supporting transcription from a DNA fragment; and
(c) a complex comprising an analyte recognizing region linked to a bacteriophage polymerase, wherein the analyte recognition region comprises a moiety selected from the group consisting of an antibody, a variable binding domain of an antibody, a binding domain of an antibody receptor, or a combination thereof;

incubating the sample in the reservoir for a time sufficient to generate transcription of the at least one reporter DNA to produce reporter RNA; and detecting the presence of reporter RNA in the reservoir wherein the presence of reporter RNA indicates that analyte is present in the sample.

* * * * *

UNITED STATES PATENT AND TRADEMARK OFFICE
CERTIFICATE OF CORRECTION

PATENT NO. : 6,238,864 B1
DATED : May 29, 2001
INVENTOR(S) : Lin Yan

It is certified that error appears in the above-identified patent and that said Letters Patent is hereby corrected as shown below:

Column 3,
Lines 11-13, the sentence beginning with "The term 'capturing agent' refers" begins a new paragraph.

Column 4,
Line 7, after "provides" insert -- an --.
Line 20, after "thereof" insert -- . --.

Column 5,
Line 27, after "preferably a" delete "DNA, that" and insert therefor -- DNA that --
Line 41, after "SEQ ID NO:3" delete ",".

Column 8,
Line 10, after "distance-," delete "orientation," and insert therefor -- orientation-, --.
Line 16, before "is the galactose" delete "system" and insert therefor -- systems --.
Line 35, the paragraph beginning "Purified gal4" is the last sentence of the previous paragraph.

Column 14,
Line 24, the sentence beginning "The pellets were dissolved" begins a new paragraph.

Column 17,
Line 37, after "RNA indicates that" delete "the".

UNITED STATES PATENT AND TRADEMARK OFFICE
CERTIFICATE OF CORRECTION

PATENT NO. : 6,238,864 B1
DATED : May 29, 2001
INVENTOR(S) : Lin Yan

It is certified that error appears in the above-identified patent and that said Letters Patent is hereby corrected as shown below:

<u>Column 19,</u>
Line 22, after "The method of claim" insert -- 22 --.

Signed and Sealed this

Fifth Day of February, 2002

Attest:

JAMES E. ROGAN
*Director of the United States Patent and Trademark Office*

*Attesting Officer*

SEQUENCE LISTING

```
<160> NUMBER OF SEQ ID NOS: 4

<210> SEQ ID NO 1
<211> LENGTH: 56
<212> TYPE: DNA
<213> ORGANISM: Artificial Sequence
<220> FEATURE:
<223> OTHER INFORMATION: Description of Artificial Sequence: Adaptor

<400> SEQUENCE: 1
ctagaggcgc gggccggaaa aaaaaaaaa aaaaaaaaa aaaaaaaagc gcggcg        56

<210> SEQ ID NO 2
<211> LENGTH: 56
<212> TYPE: DNA
<213> ORGANISM: Artificial Sequence
<220> FEATURE:
<223> OTHER INFORMATION: Description of Artificial Sequence: Adaptor

<400> SEQUENCE: 2
gatccgccgc gctttttttt tttttttttt tttttttttt tttccggccc gcgcct        56

<210> SEQ ID NO 3
<211> LENGTH: 87
<212> TYPE: DNA
<213> ORGANISM: Artificial Sequence
<220> FEATURE:
<223> OTHER INFORMATION: Description of Artificial Sequence: Adaptor
```

-continued

```
<400> SEQUENCE: 3
aattcttcgc cggatctttg tgaaggaacc atttaggtga cactatatcc gtcgactcta      60
gagggtatat aatgcgccgc tcgaaga                                         87

<210> SEQ ID NO 4
<211> LENGTH: 87
<212> TYPE: DNA
<213> ORGANISM: Artificial Sequence
<220> FEATURE:
<223> OTHER INFORMATION: Description of Artificial Sequence: Adaptor

<400> SEQUENCE: 4
agcttcttcg agcggcgcat tatataccct ctagagtcga cggatatagt gtcacctaaa      60
tggttccttc acaaagatcc ggcgaag                                         87
```